US008593275B2

(12) United States Patent
Davis

(10) Patent No.: US 8,593,275 B2
(45) Date of Patent: Nov. 26, 2013

(54) WIRELESS MONITORING SYSTEM AND METHOD WITH DUAL MODE ALARMING

(75) Inventor: Carl Claude Davis, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 323 days.

(21) Appl. No.: 13/042,885

(22) Filed: Mar. 8, 2011

(65) Prior Publication Data

US 2012/0229271 A1 Sep. 13, 2012

(51) Int. Cl.
*G08B 1/08* (2006.01)
(52) U.S. Cl.
USPC .............. 340/539.12; 340/539.11; 340/539.1; 340/573.1
(58) Field of Classification Search
USPC ........ 340/539.1, 539.12, 539.11, 573.1, 10.1, 340/10.5; 600/300, 301
See application file for complete search history.

(56) References Cited

U.S. PATENT DOCUMENTS

| 5,212,807 | A | * | 5/1993 | Chan ............................. 455/525 |
| 5,634,468 | A | * | 6/1997 | Platt et al. ..................... 600/509 |
| 5,761,245 | A | * | 6/1998 | Haukkavaara et al. ....... 375/267 |
| 7,129,836 | B2 | | 10/2006 | Lawson et al. |
| 7,301,452 | B2 | * | 11/2007 | Gerder et al. ............. 340/539.12 |
| 7,411,491 | B2 | | 8/2008 | Klabunde et al. |
| 7,606,936 | B2 | | 10/2009 | Mousseau et al. |

* cited by examiner

*Primary Examiner* — Anh V La
(74) *Attorney, Agent, or Firm* — Andrus, Sceales, Starke & Sawall, LLP

(57) ABSTRACT

A patient monitoring system and method for reliably communicating alarm conditions detected by an acquisition device that receives physiological data from the patient. The acquisition device includes a control unit that detects alarm conditions based upon the physiological data received from the patient. A primary transmitter and a secondary transmitter are coupled to the control unit and are each capable of transmitting the alarm condition. The primary transmitter is configured to connect to a wireless network and communicate over a first frequency range. The secondary transmitter is configured to transmit over a secondary wireless network using a second frequency range different from the first frequency range. When the primary transmitter is not able to communicate with the primary wireless network, the control unit activates the secondary transmitter to transmit the alarm condition. The secondary transmitter remains active until the primary transmitter reconnects with the primary wireless network.

19 Claims, 4 Drawing Sheets

WIRELESS MONITORING SYSTEM AND METHOD WITH DUAL MODE ALARMING

BACKGROUND

Patient mobility is an integral part of many patient care regimens in high acuity care environments. As part of the recovery process, patients are encouraged to periodically stand up and make short trips to the window, the bathroom, etc. Lack of patient mobility can result in physiologic complications such as deep vein thrombosis, infection and an overall prolonged recovery process.

Continuous monitoring is preferably provided during these patient mobility events. Thus, it is preferable to allow a patient to be continually monitored while not physically connected to a local/bedside monitor. Such continuous monitoring requires a reliable system for data transfer so that monitoring information is not lost or degraded. Further, if a patient is having a problem, it is desirable to know as soon as possible. For example, notice of an alarm regarding a patient condition should not be lost or delayed when the patient is moving, which could lead to a delay in care that can have a negative outcome for the patient.

While wireless data transmission can offer the advantage of substantially continuous monitoring, it is not as reliable as a direct connection. Objects may emit fields or signals that interfere with the ability of a wireless system to accurately transmit data in certain frequency ranges. For example, the Wi-Fi band, e.g., the 2.4 GHz band, is prone to collision and other interferences causing dropped packets. Further, there are often gaps in Wi-Fi networks where coverage is weak or non-existent.

Many prior art devices use the Wireless Medical Telemetry Service (WMTS) frequencies—608-614 MHz, 1395-1400 MHz, or 1429-1432 MHz—for the wireless transmission of data. The WMTS frequencies are fairly reliable because they are relatively low on the frequency spectrum and, perhaps more importantly, because they are restricted-use frequency ranges so that interference is less of an issue. However, information transmission via WMTS is slow and less practical compared to transmission via the Wi-Fi band.

As patient monitoring devices begin leveraging wireless infrastructure, such as Wi-Fi networks, it is important to make sure that the quality of patient monitoring is not degraded. With Wi-Fi connections, the quality of service and benefits of the dedicated spectrum provided by WMTS is lost. Further, with the shorter signal range and the necessity of switching between access points to stay connected, patient monitoring devices utilizing Wi-Fi must be carefully designed to ensure that monitoring quality remains high.

SUMMARY

The present disclosure stems from the inventors' research and development of improved systems and methods for increasing the reliability of alarm notification transmission and/or patient physiological data transmission in wireless patient monitoring systems. The present inventors have recognized that present monitoring systems communicating wirelessly over networks operating on non-protected frequency spectrums, such as those employing IEEE's 802.11 standards, face problems such as interference, dropped packets, competition with non-medical devices, roaming dropout, and other quality of service concerns that make it difficult or impossible to guaranty that notice of every alarm condition will be delivered quickly and accurately. In addition, the inventors recognize that using audible or local alarms as a backup can create additional problems, including alarming a patient and/or family members, and not effectively communicating the alarm condition to relevant clinicians because of their inability to hear or see the local alarm occurring in a patient room. Thus, the present inventors have recognized that wireless patient monitoring systems need to have the capability to recognize when a primary wireless communication method is failing and switch to a different communication mode that ensures communication of an alarm condition and/or patient physiological data. The present disclosure relates to improved wireless monitoring systems and methods that can reliably communicate alarm conditions and/or patient physiological data.

One embodiment relates to a patient monitoring system having an acquisition device and a secondary receiver. The acquisition device is configured to receive physiological data recorded from a patient and is comprised of a control unit configured to detect an alarm condition based on the physiological data from the patient, a primary transmitter that connects to a primary wireless network and transmits the alarm condition over the primary wireless network, and a secondary transmitter or beacon that transmits the alarm condition using a frequency range other than that used by the primary transmitter. The secondary receiver is configured to receive transmissions by the secondary transmitter or beacon. Upon the detection of an alarm condition, the acquisition device transmits the alarm condition via the primary transmitter if the primary transmitter is reliably connected to the primary wireless local area network. If the primary transmitter is not reliably connected to the primary wireless local area network, the acquisition device transmits the alarm condition via the secondary transmitter or beacon.

Another embodiment relates to an acquisition device for communicating with both a primary wireless network and a secondary wireless network, the acquisition device having a control unit, a primary transmitter, and a secondary transmitter or beacon. The control unit is configured to detect an alarm condition based on physiological data from a patient. The primary transmitter is configured to connect to the primary wireless network and transmit the alarm condition over the primary wireless network using a first frequency range. The secondary transmitter or beacon is configured to transmit the alarm condition over the secondary wireless network using a second frequency range. Upon detecting an alarm condition, the acquisition device transmits the alarm condition via the primary transmitter if the primary transmitter is reliably connected to the primary wireless network. If the primary transmitter is not reliably connected to the primary wireless network, the acquisition device transmits the alarm via the secondary transmitter or beacon.

Yet another embodiment relates to a method of transmitting an alarm condition from a patient monitoring device comprising the following steps: receiving physiological data measured from a patient, determining the presence of an alarm condition based on the physiological data, detecting whether a primary transmitter of the patient monitoring device is reliably connected to a primary wireless network when an alarm condition is present, transmitting an alarm condition using a first frequency range if the primary transmitter is reliably connected to the primary wireless network, and transmitting the alarm condition using a second frequency range if the primary transmitter is not reliably connected to the primary wireless network and an alarm condition is present. Further, the second frequency range is a different frequency range than the first frequency range.

Other principle features and advantage of the invention will become apparent to those skilled in the art upon review of the following drawings, the detailed description, and the appended claims.

DETAILED DESCRIPTION OF THE DRAWINGS

In the present description, certain terms have been used for brevity, clarity and understanding. No unnecessary limitations are to be implied therefrom beyond the requirement of the prior art because such terms are used for descriptive purposes only and are intended to be broadly construed. The different systems and methods described herein may be used alone or in combination with other systems and methods. Various equivalents, alternatives, and modifications are possible within the scope of the appended claims. Each limitation in the appended claims is intended to invoke interpretation under 35 USC §112, sixth paragraph, only if the terms "means for" or "step for" are explicitly recited in the respective limitation.

Figure 1:
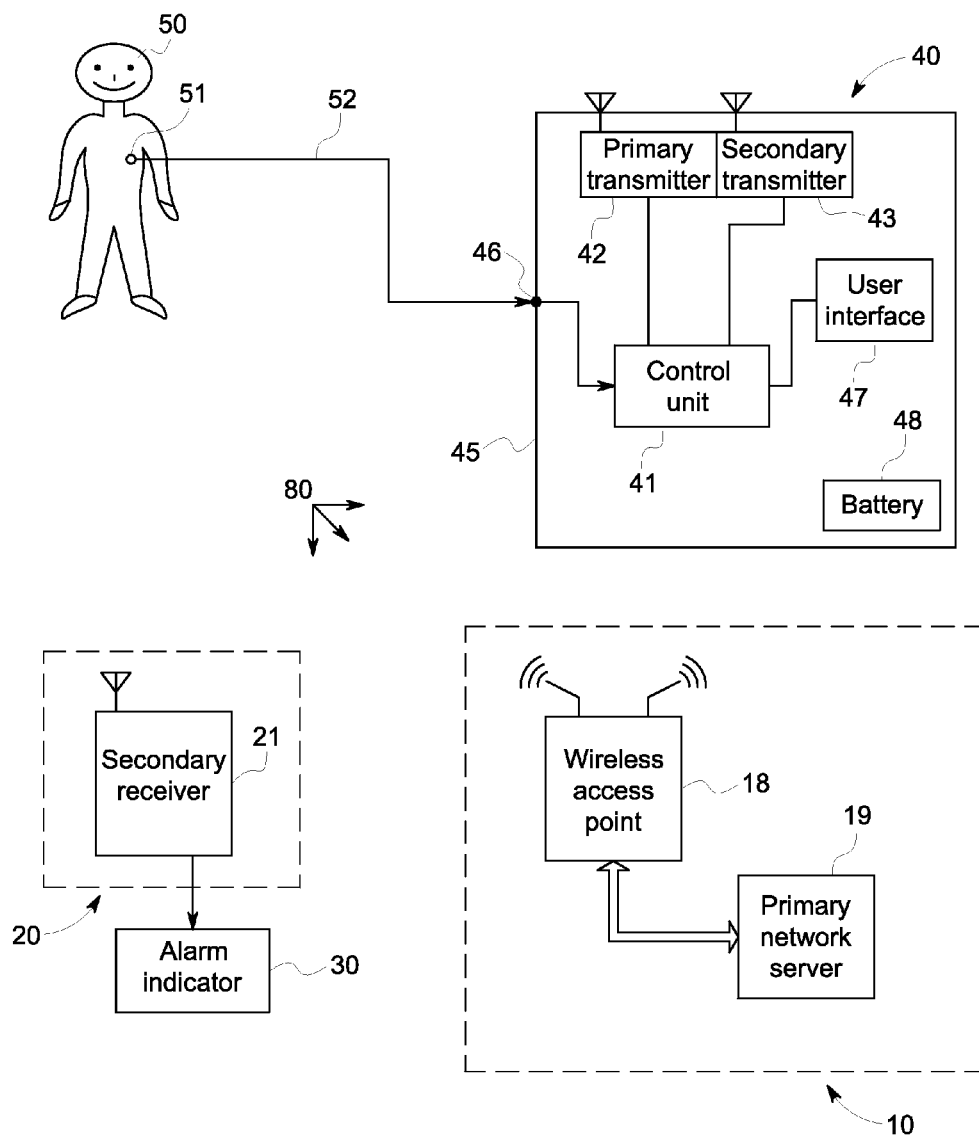
FIG. 1 is a schematic of an embodiment of a patient monitoring system with dual mode alarming.

Referring to FIG. 1, a monitoring system 80 may include an acquisition device 40 configured to detect an alarm condition and communicate that alarm condition over a primary wireless network 10 and/or a secondary wireless network 20. The acquisition device 40 receives physiological data from a patient 50, such as data gathered from one or more sensors 51 connected to the patient 50. As an illustrative example, the sensor 51 can be positioned on the patient to obtain various physiological data from the patient, such as blood pressure, temperature, heart rate or other commonly obtained physiological data. Although a single sensor 51 is illustrated, it should be understood that multiple sensors 51 could be utilized and communicate to the acquisition device 40.

The acquisition device 40 has a control unit 41 that is configured to detect an alarm condition based on the physiological data gathered from the patient 50. Upon detecting an alarm condition, the control unit 41 of the acquisition device 40 transmits the alarm over at least one of a primary wireless network 10 or a secondary wireless network 20, and the alarm condition is communicated to a clinician via one or more alarm indicators 30.

The acquisition device 40 has a primary transmitter 42 and a secondary transmitter 43. The primary transmitter 42 and the secondary transmitter 43 may be two separate devices housed in the acquisition device 40, or they may be one single device performing the functions described herein of both the primary transmitter 42 and the secondary transmitter 43.

Each of the transmitters 42 and 43 may operate on any applicable frequency range using any available technology or communication protocols—e.g., the 802.11 protocols issued by IEEE, Bluetooth™, ultrasound, infrared, WMTS, etc. However, each of the primary transmitter 42 and the secondary transmitter 43 are specifically configured to operate in either different frequency ranges from one another or using different modalities, as will be discussed below. The primary transmitter 42 and/or secondary transmitter 43 use technology that automatically detects the presence of wireless receivers in the vicinity of the communication circuit operating on the same frequency range as that device.

The primary transmitter 42 may be any type of transmitting device capable of transmitting information to a primary wireless network 10. The primary transmitter 42 may also have receiving capabilities. Thus, the primary transmitter 42 may be a transmitter; or, it may be a transponder, a transceiver, or some other device capable of transmitting and receiving information.

Likewise, the secondary transmitter 43 may be any type of transmitting device capable of transmitting information to a secondary wireless receiver 21. The secondary transmitter 43 may also have receiving capabilities. Thus, the secondary transmitter 43 may be a simple beacon or a transmitter only; or it may be a transponder, a transceiver, or some other device capable of transmitting and receiving information.

The primary wireless network 10 may consist of at least one wireless access point 18 and at least one primary network server 19. The wireless access point 18 may be any receiving device capable of receiving signals from a primary transmitter 42. The wireless access point 18 may additionally have the capability to transmit data. For example, the wireless access point 18 may transmit data to the primary transmitter 42. Thus, the wireless access point 18 may be a receiver; or, it may be a transceiver, or some other type of device having both receiving and transmitting capabilities.

The secondary wireless network 20 consists of at least one secondary receiver 21 configured to receive transmissions from a secondary transmitter 43. The secondary receiver 21 may be any receiving device capable of receiving signals from the secondary transmitter 43. In some embodiments, the secondary receiver 21 may also have transmission capabilities, and may be able to transmit data to the secondary transmitter 43. Thus, the secondary receiver 21 may be a receiver, or alternatively could be a transponder, a transceiver, or some other device having both receiving and transmitting capabilities.

Figure 2:
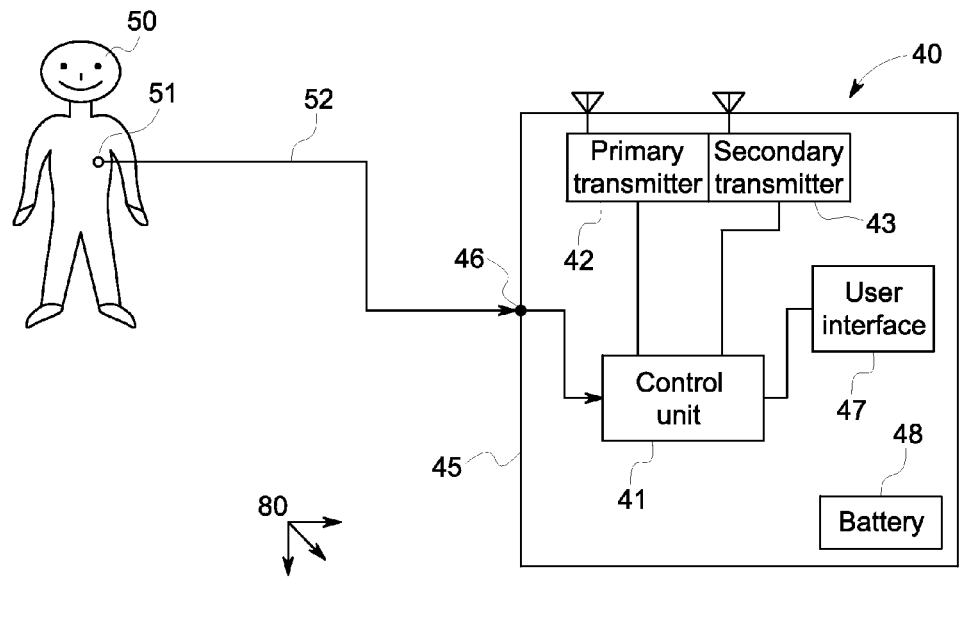
FIG. 2 is a schematic illustration of another embodiment of a patient monitoring system.
Figure 2:
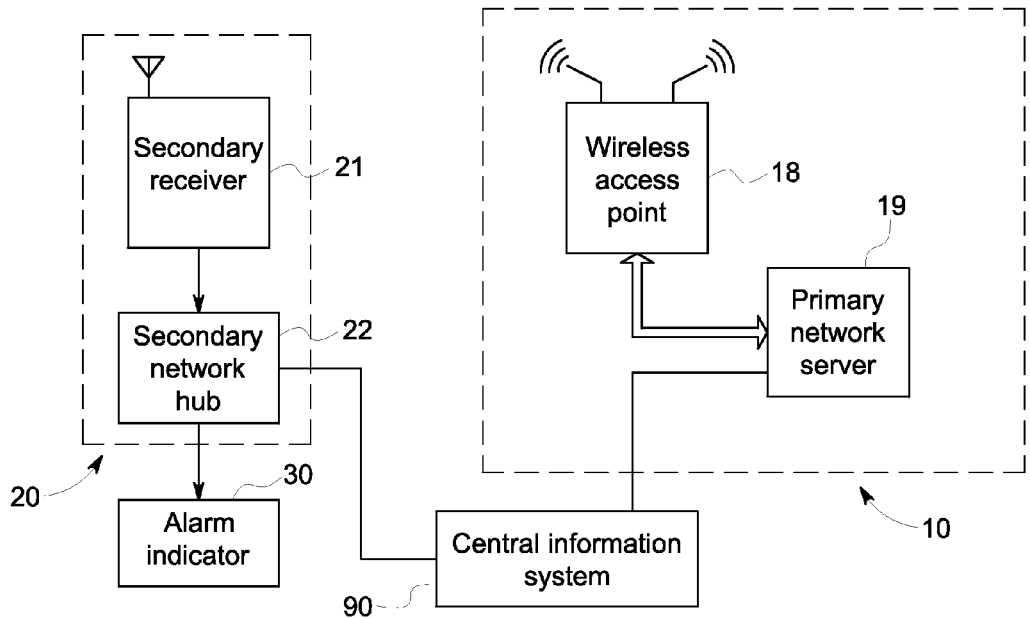
Figure 3:
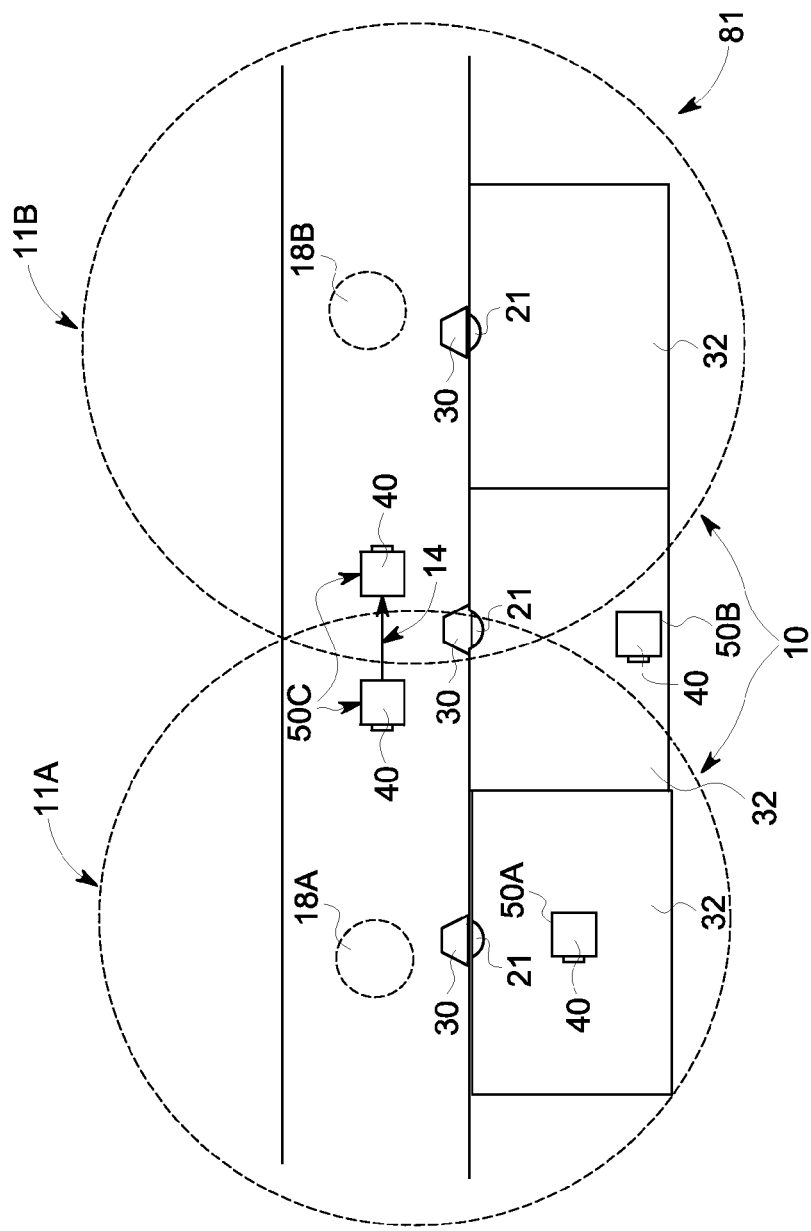
FIG. 3 depicts an exemplary hospital environment employing an embodiment of a wireless monitoring system with dual mode alarming.

In some embodiments, the secondary receiver 21 is connected to an alarm indicator 30. The alarm indicator 30 could be any device or method of indicating an alarm to a clinician. The alarm indicator 30 could be, for example, a nurse call indicator such as those already in use in patient care facilities. As shown in FIG. 3, one type of alarm indicator 30 commonly used in patient care facilities consists of a light that illuminates outside a patient's room 32. Referring back to FIG. 1, the secondary receiver 21 may be directly connected to the alarm indicator 30, such that the alarm indicator 30 would be activated by the secondary receiver 21 when the secondary receiver 21 receives an alarm notification. In another embodiment, the alarm indicator 30 could be indirectly connected to the secondary receiver 21, such that the alarm indicator 30 is activated by a system controller, such as a secondary network hub 22 or a central information system 90 as shown in FIG. 2. For example, the secondary receiver 21 may receive notice of an alarm condition and transmit that information to the secondary network hub 22. The secondary network hub 22 would then activate the alarm indicator 30 to communicate the alarm condition.

In some embodiments, the secondary network 20 consists of one secondary receiver 21 configured to receive transmissions from a secondary transmitter 43. However, in other embodiments, the secondary network 20 may consist of more than one secondary receiver 21, which may be independent of one another or networked together. As depicted in FIG. 2, the secondary network 20 may consist of one or more secondary receivers 21 connected to a secondary network hub 22. The secondary receiver 21 may be connected to a network consisting of multiple secondary receivers and may communicate with a network hub 22 and/or a centralized information system 90 at a facility. Such a central information system 90 may, for example, be in communication with or otherwise accessible from any nurses' station, and may control the alarm indicator 30 indicating an alarm condition which is detected by an acquisition device 40 and transmitted to a secondary receiver 21.

The secondary wireless network 20 may be a stand-alone network, or may be integrated partially or completely with an existing network in a patient care facility. For example, a secondary wireless network 20 could be a stand-alone network with one or more alarm indicators 30, wherein the alarm indicators inform the clinician as to the location of the relevant alarm condition. Or, the secondary wireless network 20 could be integrated with a larger central information system 90 at a healthcare facility The alarm indicator 30 may be any device, system, or means for informing a clinician of an alarm condition. The alarm indicator 30 for the secondary wireless network 20 may or may not be integrated with a central alarm indication system at a healthcare facility. The alarm indicator 30 may utilize or be integrated with an existing communication system, such as a nurse call indicator system. Alternatively, the alarm indicator 30 could be installed for the specific purpose of indicating an alarm condition detected by a patient monitoring system 80.

The alarm indicator 30 may be a physical indicator, such as a light that illuminates outside a patient's room or at a nurses' station. The alarm indicator 30 may also be integrated into a digital display system which may transmit notification to one or more digital displays located, for example, at a nurses' station. The alarm indicator 30 may also be integrated with a wireless communication system at a facility. For example, the alarm indicator 30 may propagate to handheld devices, such as pagers, cell phones, or PDAs, in the possession of clinicians.

In one embodiment, the control unit 41 of the acquisition device 40 transmits the alarm condition over the primary wireless network 10 if the primary transmitter 42 is connected to the primary wireless network 10. If the primary transmitter 42 is not connected to the primary wireless network 10, the control unit 41 transmits the alarm condition over the secondary wireless network 20 using the secondary transmitter 43.

In an alternative embodiment, the control unit 41 of the acquisition device 40 is configured to transmit an alarm condition via the secondary transmitter 43 if the primary transmitter 42 is not reliably connected to the primary wireless network 10. A reliable connection may mean that the primary transmitter 42 does not have a strong enough connection to the primary wireless network 10 to reliably transmit information via that network. The requirement for a reliable connection could be defined such that the secondary transmitter 43 is used if the primary transmitter 42 has less than a predefined signal strength connection to the primary wireless network 10. For example, the requirement for a reliable connection could be set such that the secondary transmitter 43 is used if the primary transmitter 42 has only a weak signal strength connection to the primary wireless network 10. Or, as one alternative, the requirement for a reliable connection could be set such that the secondary transmitter 43 is used any time the primary transmitter 42 has less than a medium signal strength connection.

As one illustrative example, reliable connection between the primary transmitter 42 and the primary wireless network can be established by two-way communication between the primary network server 19 and the acquisition device 40 through the wireless access point 18. If an acknowledgement of alarm or a packet of information is not provided, or a "heartbeat" between the sender and receiver is lost, the connection is deemed unreliable. The requirement for the reliable connection could be permanently set by the manufacturer, or it could be adjustably set so that individual system operators or administrators could adjust the requirement for reliable connection depending on the relevant monitoring needs.

In some embodiments, the use of the primary transmitter 42 is mutually exclusive from the use of the secondary transmitter 43. In those embodiments, the secondary transmitter 43 is used instead of the primary transmitter 42 when the primary transmitter 42 is not connected, or reliably connected, to the primary wireless network 10. Alternatively, the primary transmitter 42 and secondary transmitter 43 could be used simultaneously. For example, the control unit 41 of the acquisition device 40 could be configured to transmit an alarm condition using the primary transmitter 42 and the secondary transmitter 43, simultaneously, when the primary transmitter 42 has only a weak connection to the primary wireless network 10.

The patient monitoring system 80 may be further configured to transmit the physiological data it receives from a patient 50. Thus, in addition to notification of an alarm condition, the acquisition device 40 may transmit some or all of the physiological data it receives from a patient 50 over the primary wireless network 10 or the secondary wireless network 20. For example, the control unit 41 may utilize the primary transmitter 42 to transmit physiological data recorded from a sensor 51 attached to the patient 50. In that embodiment, the acquisition device 40 could be designed to transmit the physiological data from the patient using the secondary transmitter 43 when the primary transmitter 42 is not reliably connected to the primary wireless network 10. In embodiments in which the secondary transmitter 43 has limited output bandwidth, such as an RFID tag, the priority of the information sent would be assessed to determine which information beyond the primary alarm information is sent across the secondary wireless network 20, since the primary alarm information is the critical part of the information being sent.

In an embodiment where the acquisition device 40 is configured to transmit physiological data in addition to an alarm condition, the acquisition device 40 may utilize the secondary transmitter 43 to transmit data during an alarm condition. In this embodiment, the control unit 41 would only activate the secondary transmitter 43 if an alarm condition is detected and the primary transmitter 42 is not reliably connected to the primary wireless network 10. Alternatively, in addition to transmitting an alarm when an alarm condition is detected, the acquisition device 40 may utilize the secondary transmitter 43 to transmit physiological data at any time when the primary transmitter 42 is not reliably connected to the primary wireless network 10. In this embodiment, the control unit 41 would activate the secondary transmitter 43 any time that the primary transmitter 42 is not reliably connected to the primary wireless network 10. In that instance, the secondary transmitter 43 may be employed to transmit some or all of the physiological data received by the acquisition device 40 during the time of disconnection from the primary wireless network 10.

Further, the secondary transmitter 43 may be used to only transmit notice of an alarm condition, or the secondary transmitter 43 may be used to transmit the alarm condition in conjunction with a portion of the physiological data recorded from the patient 50. Additionally or alternatively, the secondary transmitter 43 could also be used to transmit physiological data any time that the primary wireless network was unavailable. Thus, the secondary transmitter 43 may be a simple beacon which, when turned on, indicates the existence of an alarm condition. In that embodiment, the secondary transmitter 43 could be utilized when an alarm condition is triggered and the primary transmitter 42 is not reliably connected to the primary wireless network 10. There, the secondary receiver 21 would be configured to sense the presence of the beacon transmission from the secondary transmitter 43 and to compel notification of the alarm condition via the alarm indicator 30.

Alternatively, the secondary transmitter 43 may be used to transmit physiological data in addition to an alarm condition. For example, the secondary transmitter 43 could transmit the physiological data that triggered the alarm condition along with the notice of the alarm condition. Or, the secondary transmitter 43 could be used to transmit all of the physiological data recorded from the patient 50 that could not be transmitted via the primary wireless network 10. In such an embodiment, the secondary transmitter 43 could communicate at least a portion of the physiological data recorded from the patient 50 using the frequency designated for the secondary wireless network 20. Thus, the secondary receiver 21 may be configured to receive physiological data recorded from the patient 50, in addition to receiving notification of the existence of an alarm condition. Depending on the configuration of the secondary wireless network 20, the secondary receiver 21 may then transmit the physiological data and/or the alarm condition received from the secondary transmitter 43 to the secondary network hub 22.

In one embodiment shown in FIG. 2, the secondary wireless network 20 is a network of one or more secondary receivers 21 connected to a secondary network hub 22. The secondary network hub 22 receives the transmissions picked up by the one or more secondary receivers 21 which may include physiological data recorded from a patient 50 and/or notification of an alarm condition. The secondary network hub 22 may also be connected to a central information system 90 at a patient care facility and may pass on the information received by the secondary network 20 to the central information system 90.

The acquisition device 40 is configured to receive physiological data from a patient 50. The physiological data can constitute any data regarding the physiological aspect of the patient 50, including high acuity patient parameter data such as ECG, blood pressure, cardiac output, temperature, blood oxygen saturation, respiratory rate, etc. The acquisition device 40 may receive the physiological data in any form or by any transmission means. For example, the physiological data may be received from one or more sensors 51 connected to a patient 50 and recording physiological data from that patient. In one embodiment, the acquisition device 40 includes one or more inputs 46 that receive one or more wires 52 extending from the one or more sensors 51 coupled to the patient 50.

In another embodiment, the acquisition device 40 may receive the physiological data via a wireless transmission from another device. The acquisition device 40 may receive physiological data from any device or means that recorded physiological data from the patient. For example, the acquisition device 40 could receive physiological data related to the cardiac activity of a patient from a heart monitor, where the heart monitor is a separate and independent device from the acquisition device 40. It is also contemplated that the physiological data from the patient could include direct input from a patient 50 indicating an alarm condition, such as the patient pressing an alarm button which has an output that is connected to or sensed by the control unit 41 in the acquisition device 40.

The acquisition device 40 may include a housing 45 which is configured to be small and compact and easy to transport. The housing 45 may also contain a clip or device that allows it to be wearable by a patient. Alternatively, the housing 45 may be configured to fit in a carrying case that is wearable by a patient 50.

The acquisition device 40 may include a user interface 47. The user interface 47 may comprise any user input mechanism and/or a display. The user interface 47 may include displays indicating system function and/or subject parameter data, may include notice of an event, and/or may include user inputs that allow a user to enter commands or other data. For example, the user interface 47 may include LEDs that indicate the status of the acquisition device 40, including the connection status of the primary transmitter 42 to the primary wireless network 10, the charge status of the battery, the alarm condition status, etc. The user interface 47 can also include user input devices, such as calibration tools or a means of adjusting the requirements for an alarm condition. The user interface 47 could also include a means for adjusting the threshold connectivity level that qualifies as a reliable connection between the primary transmitter 42 and the primary wireless network 10 before the secondary transmitter 43 is employed. For example, the user interface 47 could be used to set the threshold signal strength from the primary wireless network 10 below which the secondary transmitter 43 would be used to propagate patient data and/or an alarm condition. Alternatively, the user interface could be replaced or supplemented by a remote device like a central station to adjust the threshold connectivity levels such that these levels could be adjusted when the device is connected to the primary wireless network.

The acquisition device 40 may also include a battery 48. The battery 48 is preferably a rechargeable battery that powers the acquisition device 40. The battery 48 may also be configured to be removable and/or interchangeable.

The acquisition device 40 may include an expansion port that allows additional resources to be connected. For example, the acquisition device may control a device that administers therapy to a patient 50. Alternatively, the acquisition device 40 could interface with another patient monitoring device, such as an ECG device.

Referring to FIG. 3, an exemplary scenario employing an embodiment of the patient monitoring system 80 is depicted. FIG. 3 depicts an exemplary medical care facility having several patient rooms 32 and several patients 50A-50C, at least some of whom are mobile. In the depicted scenario, patients 50A-50C are each equipped with an acquisition device 40. The primary wireless network 10 includes wireless access points 18A and 18B. The secondary wireless network 20 is comprised of secondary receivers 21, placed in each of the patient rooms 32 and connected to the nurse call indicator 30. In this embodiment, the secondary transmitter 43 of the acquisition device 40 transmits a signal to the secondary receiver 21, and the secondary receiver 21 activates the nurse call indicator 30 outside of the patient room 32.

In such a situation where patients are being monitored by wireless patient monitoring systems, patients may move in or out of areas with strong wireless network coverage. For example, FIG. 3 depicts three patients 50A-50C in three different situations with respect to wireless network coverage. Patient 50A is within range 11A of the wireless access point 18A of the primary wireless network 10. Patient 50B is not within range of any wireless access point of the primary wireless network 10. Patient 50C is in motion, moving between range 11A of wireless access point 18A and range 11B of wireless access point 18B. During that transition, the primary transmitter 42 will be "roaming" in area 14, where the patient acquisition device 40 is breaking the connection between the first wireless access point 18A and establishing a new connection with a second wireless access point 18B. During that roaming stage, the primary transmitter 42 of the patient acquisition device 40 may lose connection with the primary wireless network 10 for up to several seconds. During that time, physiological data and/or an alarm condition will not be communicated over the primary wireless network 10. During that roaming period, an alarm would not be able to be communicated over the primary wireless network 10, and thus the patient acquisition device 40 would operate the secondary transmitter 43 to communicate the alarm over the secondary wireless network 20.

In one embodiment, the primary wireless network 10 is a standard wireless local area network—e.g., a Wi-Fi network operating according to the 802.11 standard from IEEE—having access points 18A-18B as standard wireless access points. In an embodiment where the primary wireless network 10 is a Wi-Fi network, and the access points 18A-18B are standard Wi-Fi access points, it is likely that areas will exist in a monitored facility 81 where the primary wireless network 10 coverage will be minimal or non-existent. In those areas, the patient monitoring system 80 would rely on the secondary wireless network 20 to transmit an alarm condition and/or physiological data recorded from a patient 50.

A secondary wireless network 20 must utilize a different frequency range than the primary wireless network 10. The secondary wireless network 20 may take on many different forms and may utilize any frequency range other than that used by the primary wireless network 10. For example, the secondary wireless network 20 may use a frequency range in the ultrasonic frequency spectrum, a frequency range in the infrared frequency spectrum, a frequency range in a cellular frequency band, etc.

In one embodiment, the secondary wireless network 20 operates in the ultrasound frequency spectrum. In that embodiment, the secondary transmitter 43 and the secondary receiver 21 would be configured to transmit and receive signals that are within the ultrasonic frequency spectrum, which is generally recognized as being between 20 KHz and 10 MHz. In this embodiment, the ultrasound receivers would be placed systematically around the monitored facility 81 such that a patient would always be within range of a secondary receiver 21, and thus the secondary wireless network 20. Since ultrasound frequencies are generally regarded as having a longer signal range at a given amplitude than higher frequencies, in some embodiment of the system, the ultrasound secondary receivers 21 may have a greater signal range than the wireless access points 18A-18B and may be placed less frequently or further apart than the wireless access points 18. Alternatively, secondary receivers 21 may be placed more frequently or closer together than the wireless access points 18 so that coverage of the secondary wireless network is very thorough, and so that even weak signals emitted by secondary transmitters 43 can be picked up by the secondary wireless network 20.

In an alternative embodiment, the secondary wireless network 20 operates in the infrared frequency spectrum. In that embodiment, the secondary transmitter 43 is configured to transmit a frequency range that is in the infrared frequency spectrum, and the secondary receiver 21 is configured to receive that same frequency range in the infrared frequency spectrum. The infrared frequency spectrum is in the terahertz range, spanning from approximately 0.3 to 400 THz. With a secondary network operating on the infrared frequency spectrum, it may be necessary to design the system such that a monitored patient 50 is always within relatively close proximity of a secondary receiver 21. For example, an infrared secondary receiver 21 may be placed in every patient room 32 with a monitored patient 50.

In another embodiment, the secondary wireless network 20 may leverage an existing network at a healthcare facility, such as a WMTS network. WMTS, or Wireless Medical Telemetry Service, operates in the frequency the ranges of 608-614 MHz, 1394-1400 MHz, and 1429-1432 MHz. WMTS networks and devices operating on WMTS networks may use network protocols such as that described in U.S. Pat. No. 5,944,659. The WMTS band is reserved almost exclusively for medical devices. Under current FCC guidelines, the WMTS spectrum is reserved only for use by medical telemetry equipment used in hospitals and healthcare facilities to transmit patient measurement data. Examples of medical telemetry equipment include heart, blood pressure, and respiratory monitors, and also the devices disclosed herein. Further, only authorized devices may operate on the WMTS spectrum and a database is maintained of all equipment approved for operation on the spectrum. Thus, the frequency does not suffer from traffic or interference caused by non-medical devices, such as consumer devices making voice or video communications.

Figure 4:
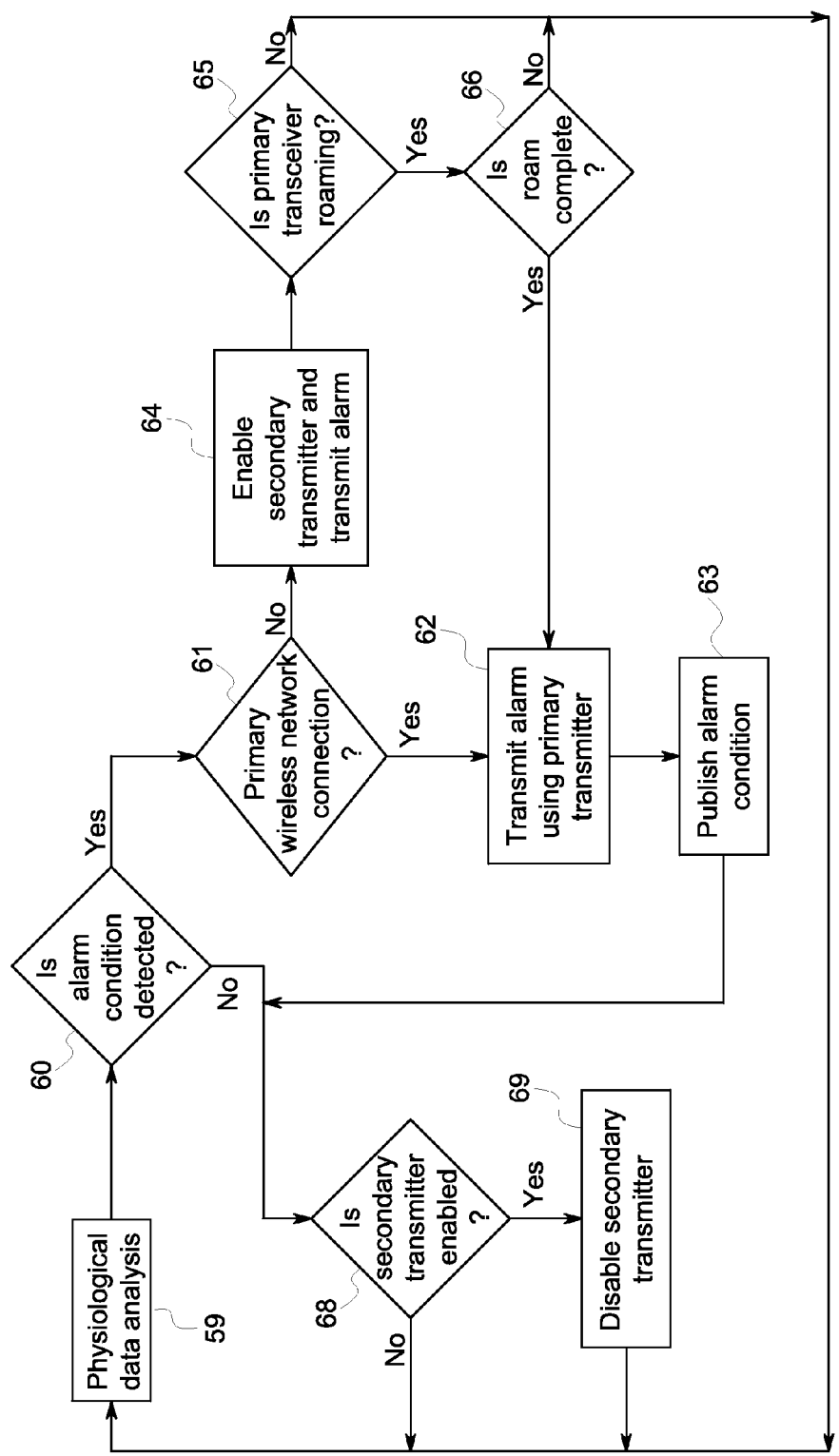
FIG. 4 is a flowchart of the steps performed by a wireless monitoring system with dual mode alarming, according to one embodiment of the invention.

Referring to FIG. 4, the flow chart depicts one embodiment of an alarm communication process, preferably performed by the control unit 41 of the acquisition device 40 shown in FIG. 1. Initially, the system determines whether an alarm condition is detected at block 60. The alarm condition is detected by the control unit 41 based on physiological data measured from the patient 50 and is analyzed at block 59. Upon detecting an alarm condition at block 60, the control unit 41 may transition to block 61 where it determines the status of the connection between the primary transmitter 42 and the primary wireless network. The determination at block 61 may be based on whether or not the primary transmitter 42 has any existing connection to a wireless access point 18. Or, the determination at block 61 can be made based on whether the primary transmitter 42 is reliably connected to the primary wireless network 10 through a wireless access point 18. A reliable connection may be defined in any number of ways, including as a connection of at least a certain signal strength.

If the control unit 41 determines that the primary transmitter 42 is reliably connected to the primary wireless network 10, then the alarm condition is transmitted at block 62 over the primary wireless network 10 using the primary transmitter 42. Data transmitted at block 62 may be published on the primary wireless network at block 63, for example by using an alarm indicator.

If the control unit 41 determines at block 61 that the primary transmitter 42 is not reliably connected to the primary wireless network 10, then the control unit 41 enables the secondary transmitter 43, block 64, and the alarm condition is transmitted over the secondary wireless network 20. Then, at block 65 a determination is made as to whether the primary transmitter 42 is roaming 14—e.g., transitioning from a connection to one wireless access point 18A to another wireless access point 18B.

If the determination at block 64 is that the primary transmitter is not roaming 14, then the control unit 41 returns to performing data analysis at block 59. At this point, the secondary transmitter 43 is still enabled. Returning to block 59, data analysis is performed to see if the alarm condition persists. If an alarm condition is still detected at block 60, then the process repeats. The secondary transmitter 43 stays enabled until one of two conditions are met: either the alarm condition termination, block 60 to 68, or a connection is established with the primary wireless network, block 61-62.

If the determination is made at block 64 that the primary transmitter 42 is roaming 14, then the control unit 41 may check the roaming 14 status once more at block 66. Since a roaming 14 state may last less than one second, it may be preferable to re-check the status of the alarm condition, as depicted in the embodiment of FIG. 4. If, upon re-check, the primary transmitter 42 is still roaming 14, then the control unit 41 returns to performing data analysis at block 59. Returning to block 59, data analysis is performed to see if the alarm condition persists. If an alarm condition is still detected at block 60, then the entire process repeats. The secondary transmitter 43 stays enabled until one of two conditions are met: either the alarm condition termination, block 60 to 68, or a connection is established with the primary wireless network, block 61-62.

At block 66, if the roaming 14 cycle has ended and the primary transmitter 24 has established connection with a wireless access point 18, then the alarm may be transmitted using the primary transmitter, block 62, and the alarm condition published, block 63. At that point, the secondary transmitter 43 is disabled, block 68-69, and the control unit 41 returns to performing data analysis at block 59.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A patient monitoring system, comprising:
   an acquisition device configured to receive physiological data from a patient, the acquisition device comprising:
      a control unit configured to detect an alarm condition based on the physiological data from the patient;
      a primary transmitter configured to connect to a wireless network and transmit the alarm condition over the wireless network; and
      a secondary transmitter configured to transmit the alarm condition using a frequency range other than that used by the primary transmitter; and
   a secondary receiver configured to receive transmissions from the secondary transmitter,
   wherein, upon detecting an alarm condition, the acquisition device transmits the alarm condition via the primary transmitter if the primary transmitter is connected to the primary wireless network and transmits the alarm condition via the secondary transmitter if the primary transmitter is not connected to the primary wireless network.

2. The system of claim 1, wherein, upon detecting an alarm condition, the acquisition device transmits the alarm condition via the secondary transmitter only if the primary transmitter is not reliably connected to the primary wireless network.

3. The system of claim 1, further comprising an alarm indicator configured to communicate the alarm condition received by the secondary receiver.

4. The system of claim 1, wherein the wireless network is a wireless local area network including at least one wireless access point.

5. The system of claim 1, wherein the secondary receiver is an ultrasound receiver and the secondary transmitter is configured to transmit the alarm condition using a frequency range that is within an ultrasound frequency spectrum.

6. The system of claim 1, wherein the secondary receiver is an infrared receiver and the secondary transmitter is configured to transmit the alarm condition using a frequency range that is within an infrared frequency spectrum.

7. The system of claim 1, wherein the primary transmitter and secondary transmitter are one device.

8. The system of claim 1, wherein the secondary transmitter is further configured to transmit at least a portion of the physiological data and the secondary receiver is configured to receive at least a portion of the physiological data from the secondary transmitter.

9. The system of claim 8, wherein the acquisition device transmits the physiological data using the secondary transmitter when the primary transmitter is not reliably connected to the primary wireless network.

10. An acquisition device configured to receive physiological data from a patient and for communicating with both a primary wireless network and a secondary wireless network, the acquisition device comprising:
    a control unit, configured to detect an alarm condition based on the physiological data received from the patient;
    a primary transmitter configured to connect to the primary wireless network and transmit the alarm condition over the primary wireless network using a first frequency range; and
    a secondary transmitter configured to transmit the alarm condition over the secondary wireless network using a second frequency range; and
    wherein the first frequency range and the second frequency range are different frequency ranges; and
    wherein upon detecting an alarm condition, the acquisition device transmits the alarm condition via the primary transmitter if the primary transmitter is reliably connected to the primary wireless network and transmits the alarm condition via the secondary transmitter only if the primary transmitter is not reliably connected to the primary wireless network.

11. The system of claim 10, further comprising an alarm indicator connected to the secondary wireless network and configured to communicate the alarm condition.

12. The system of claim 10, wherein the second frequency range is within an ultrasound frequency spectrum.

13. The system of claim 10, wherein the second frequency range is within an infrared frequency spectrum.

14. The system of claim 10, wherein the secondary transmitter is further configured to transmit at least a portion of the physiological data over the secondary wireless network.

15. The system of claim 14, wherein the acquisition device transmits the physiological data using the secondary transmitter when the primary transmitter is not reliably connected to the primary wireless network.

16. A method of transmitting an alarm condition from an acquisition device, comprising:
    receiving physiological data measured from a patient in the acquisition device;
    determining the presence of an alarm condition in the acquisition device based on the received physiological data;

detecting whether a primary transmitter of the acquisition device is reliably connected to a primary wireless network when the alarm condition is present;

utilizing the primary transmitter to transmit the alarm condition using a first frequency range if the primary transmitter is reliably connected to the primary wireless network; and utilizing a secondary transmitter to transmit the alarm condition using a second frequency range if the primary transmitter is not reliably connected to the primary wireless network and an alarm condition is present, wherein the second frequency range is in a different frequency spectrum than the first frequency range.

17. The method of claim 16, further including the step of continuing transmission of the alarm condition using the second frequency range until the primary transmitter is connected to the primary wireless network or the alarm condition is terminated.

18. The method of claim 16, wherein the secondary frequency range is within an ultrasound frequency spectrum.

19. The method of claim 16, wherein the secondary frequency range is within an infrared frequency spectrum.

* * * * *